United States Patent
Goel et al.

(10) Patent No.: US 11,642,178 B2
(45) Date of Patent: May 9, 2023

(54) GUIDEWIRE

(71) Applicant: CENTERLINE BIOMEDICAL, INC., Cleveland, OH (US)

(72) Inventors: Vikash R. Goel, Cleveland, OH (US); Naoki Ooka, Gunma (JP)

(73) Assignee: CENTERLINE BIOMEDICAL, INC., Cleveland, OH (US)

( * ) Notice: Subject to any disclaimer, the term of this patent is extended or adjusted under 35 U.S.C. 154(b) by 145 days.

(21) Appl. No.: 17/108,587

(22) Filed: Dec. 1, 2020

(65) Prior Publication Data

US 2021/0244483 A1 Aug. 12, 2021

Related U.S. Application Data

(60) Provisional application No. 62/971,651, filed on Feb. 7, 2020.

(51) Int. Cl.
*A61B 34/20* (2016.01)

(52) U.S. Cl.
CPC ...... *A61B 34/20* (2016.02); *A61B 2034/2051* (2016.02); *A61B 2034/2074* (2016.02)

(58) Field of Classification Search
CPC ............ A61B 34/20; A61B 2034/2051; A61B 2034/2074; A61M 2025/0915; A61M 2025/09175; A61M 25/09; A61M 2025/09083
See application file for complete search history.

(56) References Cited

U.S. PATENT DOCUMENTS

| | | | |
|---|---|---|---|
| 5,282,478 A | 2/1994 | Fleischhaker, Jr. et al. |
| 5,313,967 A | 5/1994 | Lieber et al. |
| 6,156,046 A | 12/2000 | Passafaro et al. |
| 6,428,489 B1 | 8/2002 | Jacobsen |

(Continued)

FOREIGN PATENT DOCUMENTS

| EP | 1239901 B1 | 10/2007 |
|---|---|---|
| JP | 2016150254 A | 8/2016 |

(Continued)

OTHER PUBLICATIONS

Applicant: Centerline Biomedical, Inc.; "Guidewire"; International Application No. PCT/US2021/016287; PCT International Search Report and Written Opinion; Authorized Officer Inho Han; dated May 14, 2021; 12 pgs.

(Continued)

*Primary Examiner* — Joel Lamprecht
(74) *Attorney, Agent, or Firm* — Tarolli, Sundheim, Covell & Tummino LLP

(57) ABSTRACT

A guidewire, which can be used with a surgical navigation system, is provided. An elongate tube body defines a tube lumen and has longitudinally spaced proximal and distal body ends. The tube body includes a first longitudinal biasing portion including at least one first-direction helical cut therealong. The tube body also includes a second longitudinal biasing portion, including at least one second-direction helical cut therealong. The first direction is radially opposite the first direction. A core wire is at least partially located inside the tube lumen and has longitudinally spaced proximal and distal core wire ends. A tracking sensor is located at least partially within the tube lumen.

22 Claims, 3 Drawing Sheets

(56) References Cited

U.S. PATENT DOCUMENTS

| | | | |
|---|---|---|---|
| 7,914,466 B2 * | 3/2011 | Davis | A61M 25/0054 600/585 |
| 8,292,827 B2 | 10/2012 | Musbach et al. | |
| 8,460,214 B2 | 6/2013 | Kuban | |
| 8,845,675 B2 | 9/2014 | Johnson et al. | |
| 9,254,143 B2 | 2/2016 | Huynh et al. | |
| 9,943,668 B2 | 4/2018 | Jahrmarkt | |
| 10,271,793 B2 * | 4/2019 | Vanney | A61B 5/6851 |
| 10,315,018 B2 | 6/2019 | Eidenschink et al. | |
| 10,561,820 B2 | 2/2020 | Sullivan et al. | |
| 10,709,312 B2 | 7/2020 | Stigall et al. | |
| 10,799,145 B2 | 10/2020 | West et al. | |
| 2006/0074318 A1 | 4/2006 | Ahmed et al. | |
| 2006/0100687 A1 | 5/2006 | Fahey et al. | |
| 2007/0112371 A1 | 5/2007 | Cangialosi et al. | |
| 2009/0306587 A1 | 12/2009 | Milijasevic et al. | |
| 2014/0187980 A1 | 7/2014 | Burkett | |
| 2014/0214007 A1 | 7/2014 | Kimura | |
| 2015/0148693 A1 | 5/2015 | Burkett | |
| 2015/0250981 A1 | 9/2015 | Beasley et al. | |
| 2015/0374523 A1 | 12/2015 | West | |
| 2016/0310079 A1 | 10/2016 | Vanney et al. | |
| 2018/0228502 A1 | 8/2018 | Shaffer et al. | |
| 2019/0192828 A1 | 6/2019 | Gupta | |
| 2019/0282170 A1 | 9/2019 | Vanney et al. | |
| 2019/0329031 A1 | 10/2019 | Ma et al. | |
| 2019/0357936 A1 | 11/2019 | To et al. | |
| 2019/0374745 A1 | 12/2019 | Giles | |
| 2020/0093351 A1 | 3/2020 | Harlan | |
| 2020/0222664 A1 | 7/2020 | Cottone et al. | |

FOREIGN PATENT DOCUMENTS

| | | |
|---|---|---|
| WO | 00/24451 A2 | 5/2000 |
| WO | 2004093655 A3 | 11/2004 |
| WO | 2018156498 A1 | 8/2018 |
| WO | 2019195287 A1 | 10/2019 |

OTHER PUBLICATIONS

Applicant: Centerline Biomedical, Inc.; Indian Application No. 202247041808 Filed Jul. 21, 2022; Indian Examination Report; dated Nov. 10, 2022; 6 pgs.

* cited by examiner

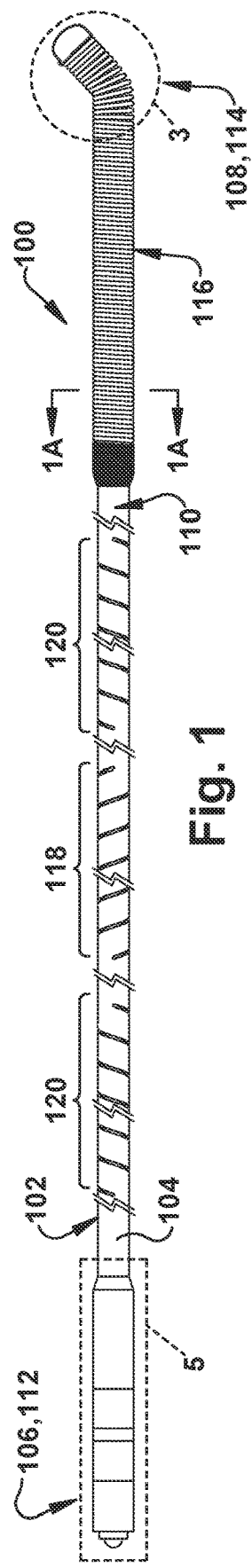
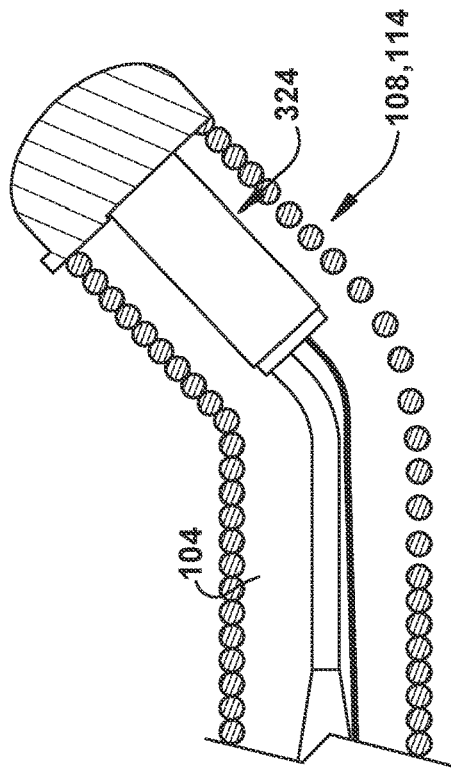
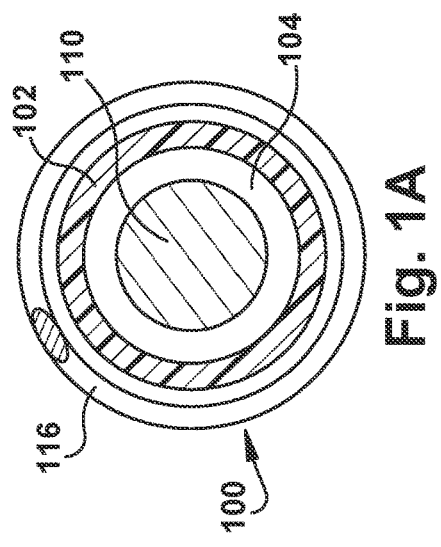
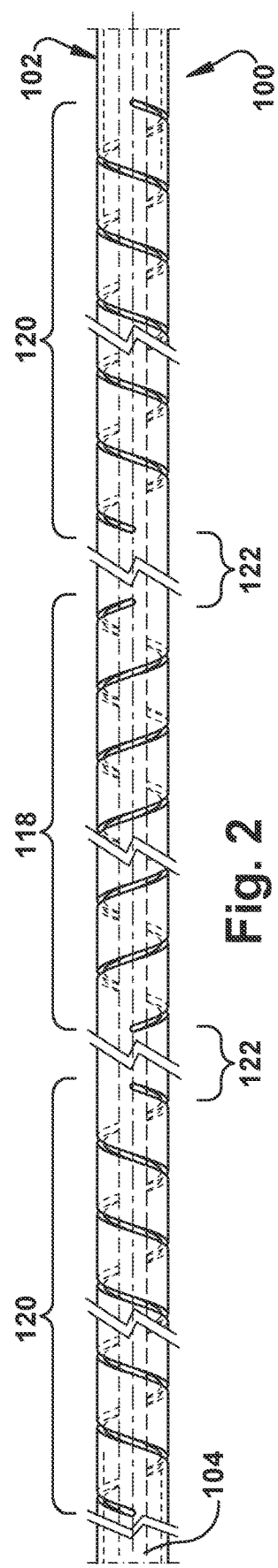

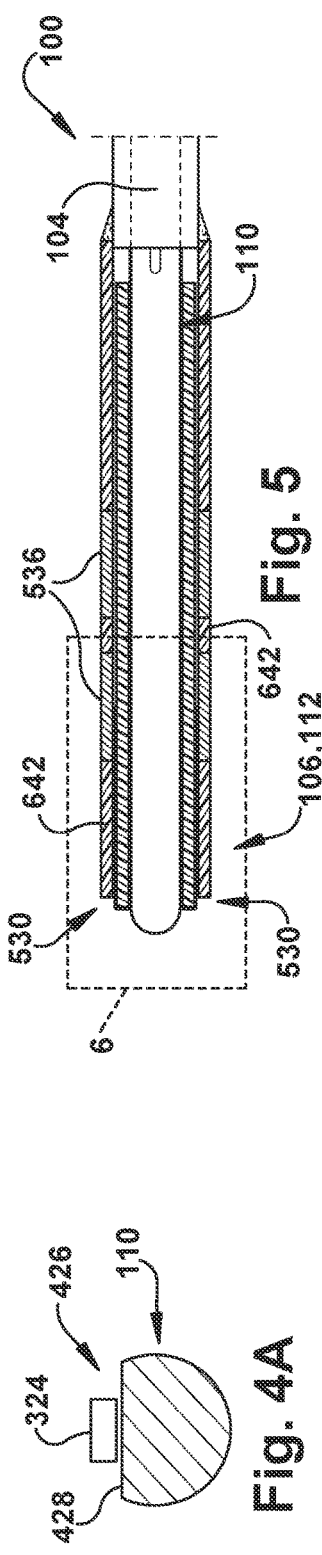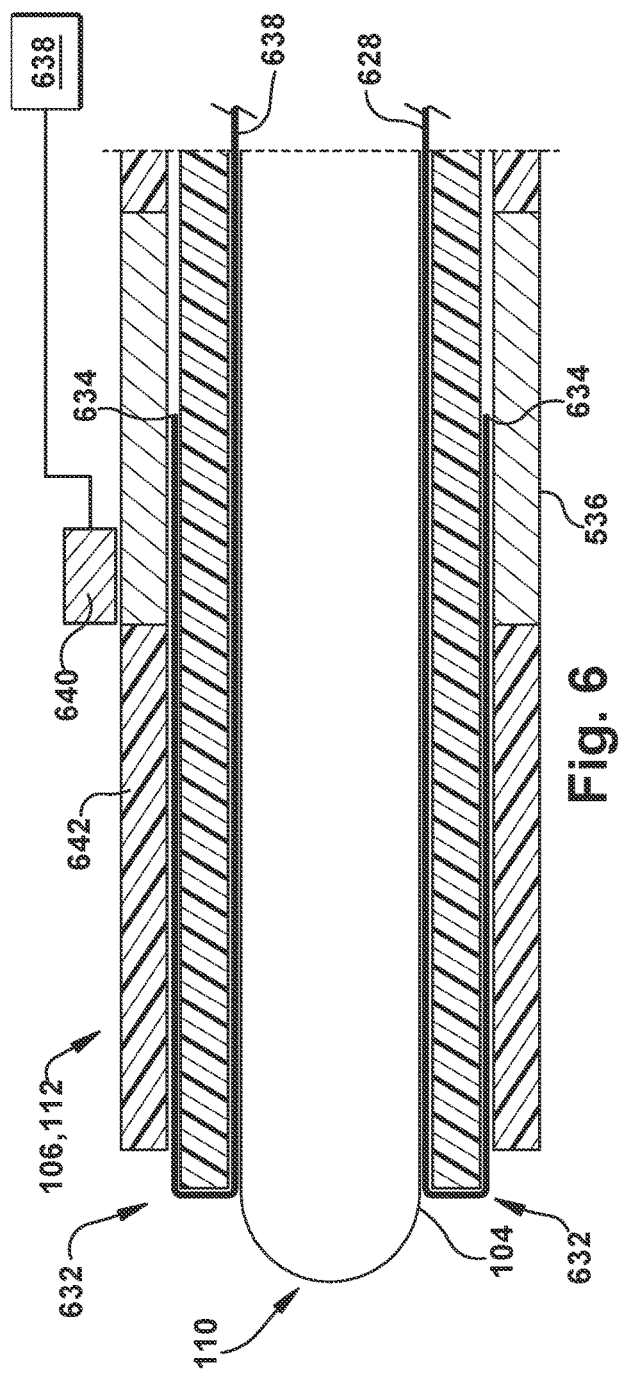

though the outer coil 116 could be made of stainless
GUIDEWIRE

CROSS-REFERENCE TO RELATED APPLICATION

This application claims priority from U.S. Provisional Application No. 62/971,651, filed 7 Feb. 2020, the subject matter of which is incorporated herein by reference in its entirety.

TECHNICAL FIELD

This disclosure relates to an apparatus and method for use of a surgical navigation system and, more particularly, to a method and apparatus of a guidewire capable of providing an indication of its position in space to a surgical navigation system.

BACKGROUND

In order to perform as desired, the design of interventional guidewires used in minimally-invasive surgery should have mechanical characteristics which provide the operator with effective ability to control the device to navigate to the intended target without causing insult to the anatomy being traversed. In the process of mechanical design it is frequently necessary to strike a balance between opposing goals.

For example, a guidewire may need to exhibit both flexibility (the ability to bend on its longitudinal axis) and torqueability (the ability to transmit rotational force) in order to be able to atraumatically navigate tortuous blood vessels. However, many aspects of mechanical design which achieve one can compromise the other. Moreover, the flexibility may need to be variable over the length of the device. Existing guidewire designs may use a wire coil or braid surrounding a core wire to achieve the desired mechanical properties for navigation.

SUMMARY

In an aspect, a guidewire is provided. An elongate tube body defines a tube lumen and has longitudinally spaced proximal and distal body ends. The tube body includes a first longitudinal biasing portion including at least one first-direction helical cut therealong. The tube body also includes a second longitudinal biasing portion, including at least one second-direction helical cut therealong. The first direction is radially opposite the first direction. A core wire is at least partially located inside the tube lumen and has longitudinally spaced proximal and distal core wire ends. A tracking sensor is located at least partially within the tube lumen.

In an aspect, a surgical navigation system is provided. A guidewire includes an elongate tube body defining a tube lumen and having longitudinally spaced proximal and distal body ends. The tube body includes a first longitudinal biasing portion, including at least one first-direction helical cut therealong. The tube body also includes a second longitudinal biasing portion, including at least one second-direction helical cut therealong. The first direction is radially opposite the first direction. The guidewire includes a core wire, at least partially located inside the tube lumen and having longitudinally spaced proximal and distal core wire ends. The guidewire includes a tracking sensor located at least partially within the tube lumen and configured to provide a sensor signal. A communication device is electrically coupled to the tracking sensor to receive the sensor signal. The surgical navigation system is configured to generate one or more output visualizations in a user-perceptible format.

BRIEF DESCRIPTION OF THE DRAWINGS

For a better understanding, reference may be made to the accompanying drawings, in which:

FIG. 1 is a side view of an example aspect of the invention;

FIG. 1A is a schematic cross-sectional view taken along line "1A-1A" of FIG. 1;

FIG. 2 is a schematic side view of a component of the aspect of FIG. 1;

FIG. 3 is a partial cross-sectional side view of area "3" of FIG. 1;

FIG. 4 is a partial side view of a component of the aspect of FIG. 1;

FIG. 4A is a schematic cross-sectional view taken along line "4A-4A" of FIG. 4;

FIG. 5 is a partial cross-sectional side view of area "5" of FIG. 1;

FIG. 6 is a schematic cross-sectional side view of area "6" of FIG. 5; and

DESCRIPTION OF ASPECTS OF THE DISCLOSURE

Figure 7:
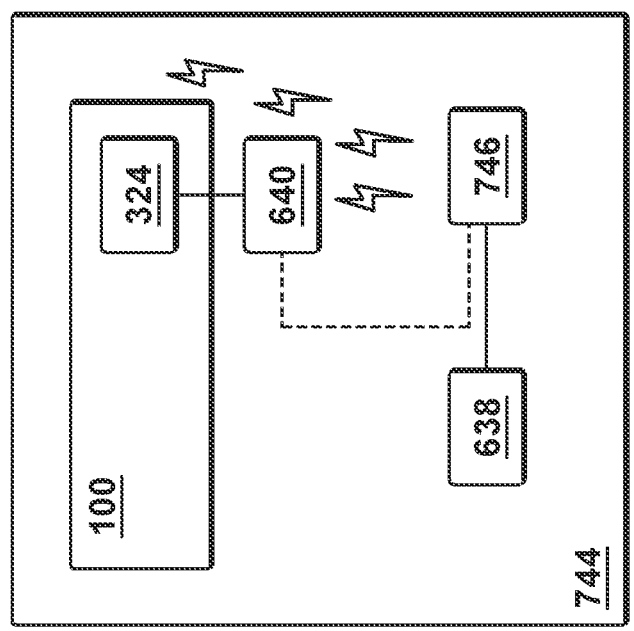
FIG. 7 is a schematic depiction of a system including the aspect of FIG. 1.

FIG. 1 depicts a guidewire 100 apparatus. The guidewire 100 includes an elongate tube body 102 defining a tube lumen 104 and having longitudinally spaced proximal and distal body ends 106 and 108, respectively. The tube body 102 could be made of stainless steel, polymers, nitinol, any other suitable material, or any combination thereof.

A core wire 110 may be at least partially located inside the tube lumen 104, as shown in FIG. 1A. The core wire 110 has longitudinally spaced proximal and distal core wire ends 112 and 114, respectively. The core wire 110 could be made of stainless steel, polymers, nitinol, any other suitable material, or any combination thereof.

An outer coil 116 may at least partially surround the tube body 102 adjacent the distal tube end 108, again as shown in FIG. 1A The outer coil 116 could be made of stainless steel, polymers, nitinol, any other suitable material, or any combination thereof. The outer coil 116 may be fixed to the tube body 102, such as by an adhesive, welding, friction fitting or the like.

As shown in FIG. 2, the tube body 102 includes a first longitudinal biasing portion 118 having at least one first-direction helical cut therealong and a second longitudinal biasing portion 120 having at least one second-direction helical cut therealong. The first direction is radially opposite the first direction. That is, the "handedness" or "sense" of the rotation of the helical cuts are opposite for the first and second directions, which is termed "radially opposite" herein. This "handedness" concept is also known as "chirality", in some contexts.

There can be as many, or as few, first and second longitudinal biasing portions 118 and 120 provided to the tube body 102, and located therealong, as desired for a particular use environment. The first and second longitudinal biasing portions 118 and 120, regardless of number and/or configuration, could be formed from a single integral piece of tube stock and/or assembled from a group of separate subcomponents. The first and second longitudinal biasing portions 118 and 120 are provided to assist with at least one of flexibility and torqueability of the guidewire 100. When different numbers of first and second longitudinal biasing portions 118 and 120 are provided to a single guidewire 100, the guidewire 100 will be biased to steer in a particular direction, which could be desirable in some use environments. The first and second longitudinal biasing portions 118 and 120 may be longitudinally spaced with respect to one another, or could be substantially contiguously cut along the tube body 102.

As shown in FIG. 2, a transition longitudinal portion 122 could be longitudinally interposed between selected ones (which may be adjacent ones) of the first and second longitudinal biasing portions 118 and 120, the transitional longitudinal portion(s) including no helical cuts therealong. The first biasing, second biasing, and transitional longitudinal portions 118, 120, and 122 could be of any desired lengths, and located anywhere along the tube body 102, as desired for a particular use environment. The pitch of the first and second longitudinal biasing portions 118 and 120 could be varied—either within the same first and/or second longitudinal biasing portion(s) 118 and 120 or between different first and/or second longitudinal biasing portions 118 and 120—to provide more (tighter pitch/shorter span between adjacent turns) or less (looser pitch/longer span between adjacent turns) flexibility to the guidewire 100.

Turning to FIG. 3, at least one electronic component 324 may be located at least partially within the tube lumen 104. The electronic component 324 may be a sensor (for physical properties including, but not limited to, position, temperature, and pressure), an electromagnetic coil sensor, a transducer or other signal-producing device (such as, but not limited to, an RF or Bluetooth transceiver), any other type of electronic component, or any combination thereof. In one example, the one or more electronic component 324 is an electromagnetic sensor (e.g., a sensor coil) configured to sense a plurality of degrees of freedom (DOF) in response to an electromagnetic field, such as provided by a field generator of the Aurora electromagnetic tracking system commercially available from Northern Digital Inc. of Waterloo, Ontario, Canada. A DOF-sensing electronic component 324—whether the sensor itself determines a position in space or whether the sensor provides electrical signals to an outside processor for determining the position of the sensor—is referred to as a "tracking sensor" herein. In an example, the electronic component 324 is a 5 or 6 DOF tracking sensor, including an electrically conductive coil, which provides an electrical signal (e.g., current) responsive to an electromagnetic field from a field generator.

Each electronic component 324, when present, may be mounted to a predetermined mounting area 426 along the core wire 110, such as shown in FIG. 4. The predetermined mounting area 426 may be a reduced-diameter and/or at least partially flatted portion of the core wire 110, as shown in the cross-sectional schematic view of FIG. 4A. For example, if the electronic component 324 is to be glued or otherwise affixed to the core wire 110, having a relatively planar "plateau" portion 428 of the core wire 110 (i.e., "flatted") can assist with adhesion, as compared to placing a substantially planar electronic component 324 tangent to a curved outer circumference of the core wire 110. One or more predetermined mounting areas 426, including any desired amount of flatted plateau portion 428, may be located at any desired position along the core wire 110, and may be, but are not necessarily, in radial alignment about a circumference of the core wire 110 with any other predetermined mounting area. In some use environments, an electronic component 324 may be absent, temporarily or permanently, from a chosen predetermined mounting area 426, or a chosen electronic component 324 may be placed in different predetermined mounting areas 426 for different implementations of the guidewire 100. In other examples, the electronic component 324 may be mounted at other locations within the tube lumen 104, such as mounted to an interior sidewall of the tube body 102 or mounted between the core wire 110 and the tube body.

As shown in FIGS. 5-6, at least one signal wire 628 (two shown) may be provided for carrying communication and/or power signals to and/or from the electronic component 324. Each signal wire 628 has a distal signal wire portion electrically coupled with the electronic component 324, and a proximal signal wire portion 530 located adjacent the proximal core wire end 112. The proximal signal wire portion 530 includes a U-shaped connection portion 632 which has portions simultaneously laterally inside and outside the tube lumen 104. The "lateral" direction is used herein to reference a direction toward and away from a central axis of longitudinal axis of the guidewire 100. A terminating end 634 of the proximal signal wire portion 530 is attached to an outer surface of the tube body 102, such as shown in FIG. 6. The length of each signal wire 628 may include a covering of an insulating material (e.g., plastic or rubber-like polymers) along its length.

Stated differently, the signal wire(s) 628 extend proximally from the electronic component 324 in a space between the core wire 110 and an inner wall of the tube lumen 104. The signal wire 628 may be floating freely in that toroidal space, or could be connected to one or more adjacent structures (e.g., to the core wire or interior sidewall). In an example, the signal wire 628 is wound about the core wire, such as wound along its length in a helical or spiral manner. When the proximal signal wire portion 530 reaches the proximal body end 106, the signal wire 628 is "wrapped" around from the tube lumen 104 to an ambient space, making a "hairpin" turn about a proximal-most face of the proximal body end 106, as shown in FIG. 6.

Then, the terminating end 634 of the proximal signal wire portion 530 may be compressed against the outer surface of the tube body 102 by a conductive collar 536. The compression can be a "crimping", intended to mechanically maintain the proximal signal wire portion 530 in place, or could be more of an electrical connection than a mechanical one. The conductive collar 536 can extend about a portion or all of a circumference of the tube body 102, and may be constructed at least partially of copper, silver, steel, or any other desired electrically conductive material(s), although it is contemplated that at least a portion of the conductive collar 536 will be electrically conductive for most use environments.

As shown in FIG. 5, multiple conductive collars 536 may be provided, with each conductive collar 536 being associated for signal communication with a respective signal wire 628. Any other signal wires in the vicinity (such as those passing underneath that selected conductive collar 536 toward another conductive collar 536) could be insulated so as not to inadvertently convey a signal to the selected conductive collar 536. For example, each signal wire 628 may be freed of its insulating cover (e.g., by stripping) at its respective ends for electrically connecting concurrently with both the electronic component 324 and the conductive collar 536.

In another example, the electronic component 324 may include a wireless transmitter, receiver or a transceiver to communicate with an external device or system. In such an implementation, at least one signal wire may be omitted from the structure.

In a further example, such as particularly shown in FIG. 6, at least one insulating spacer 642 could be provided between adjacent conductive collars 536 or adjacent a single conductive collar 536. In addition to providing electrical isolation between the adjacent conductive collars 536, the spacer may also present a substantially constant outer profile to the guidewire 100 instead of having a stepped outer profile due to the periodic presence of the larger-diameter conductive collars 536. The insulating spacer 642, when present, can also help to protect the areas of the proximal signal wire portion 530 which are located outside the tube lumen 104. It is also contemplated that the outer surface of the guidewire 100 could include any desired coating (e.g., a lubricious coating) and/or external sheath component(s) as desired for a particular use environment.

There also may be any desired seals, gaskets, connectors, and/or other components provided to the guidewire as appropriate for a particular use environment, and can readily be provided by one of ordinary skill in the art taking into account, for example, durability, affordability, sterilizability, ease of manufacture, and/or any other desired factors or combinations thereof.

The conductive collar 536 is configured to selectively convey electrical signals between the proximal signal wire portion 530 and an external guidewire control system, shown schematically at 638, for any desired reason and using any desired configuration. For example, a system connector, shown schematically at 640, could be used in a "slip ring" type manner to allow rotation of the conductive collar 536 (and thus the remaining components of guidewire 100) relative to the system connector 640. This slip ring operation can help avoid loss of signal communication with the electronic component 324 during normal rotational motions encountered during operation of the guidewire 100.

As an example, the system connector 640 provides an interface to electrically connect the signal wire 628 to an external device. For the example where the component is a sensor, the external device may include circuitry configured to amplify and digitize signals from the sensor. The amplified and digitized signals may be communicated from the device to a control unit that is configured to process the signal according to application requirements. In an example, the control unit is configured to compute the position and orientation of a coil sensor based on signals induced in the coil sensor from an electromagnetic field generator and provide the computed data to a computer for additional processing. In other examples, different types of signal processing and analysis from other types may be implemented by external electronics and computing systems.

FIG. 7 schematically illustrates an example implementation of the arrangement described above and generally depicted in FIG. 6. In FIG. 7, the guidewire 100 of FIGS. 1-6 is illustrated as having been incorporated into a surgical navigation system 744. In FIG. 7, an outside communication device (which may incorporate and/or be associated with the aforementioned external device, control unit, and/or guidewire control system 638) is shown schematically at 746. The outside communication device is in communication with the electronic component 324. In an example, the communication device communicates wirelessly with at least one electronic component 324 (e.g., a tracking sensor), as represented by the "lightning bolt" symbol. In another example, an annular connector 640, for example, a slip ring, could also or instead be used, as described above, to pass signals of any desired type through a respective communication link between the outside communication device 746 and at least one electronic component 324, as represented by the dashed line therebetween in FIG. 7. In other examples, the communication between each electronic component 324 and the outside communication device 746 can occur via a physical link (e.g., electrically conductive or optical link).

As a further example, the navigation system 744 is implemented similar to the navigation system disclosed in U.S. Patent Pub. No. 2014/0276002, which is incorporated herein by reference. For example, the navigation system 744 includes the communication device 746 implemented as a tracking system that includes a field generator to provide an electromagnetic field. The tracking system is coupled to the electronic component (e.g., tracking sensor) 324 through a communications link, as described herein (e.g., physical or wireless link). In an example, the tracking system 746 is electrically coupled to one or more conductive collars 536 of the guidewire 100 to receive electrical signals (e.g., current) from the tracking sensor responsive to an electromagnetic field produced by the field generator. In another example, the tracking system may provide a signal to the tracking sensor through the communication link that generates a field that is sensed by the tracking system. The tracking system 746 is configured to determine a position and orientation of the tracking sensor in a three-dimensional coordinate system of the tracking system responsive to the electrical signal from the tracking sensor.

The navigation system 744 thus can generate one or more three-dimensional user-perceptible virtual displays of patient anatomical geometry (e.g., including the geometry of patient vasculature, such as major blood vessels) and the guidewire 100 in real-time to facilitate intraoperative positioning of the guidewire 100 relative to patient anatomy. The guidewire 100 would correspond to an example of an object that is being tracked and visualized on a display of the navigation system 746.

For example, the guidewire 100 may be utilized in combination with a system to enable intraoperative positioning, such as that disclosed in the above-incorporated U.S. Patent Pub. No. 2014/0276002. The guidewire 100 may include an electromagnetic component 324 (e.g., a tracking sensor) that is used to track the position and orientation of the sensor and guidewire in three-dimensional space and to generate one or more output visualizations in a user-perceptible format, in any desired manner.

In an example, the outside communication device 746 may be electrically coupled with a tracking sensor (i.e., electronic component 324) to receive a sensor signal, and the surgical navigation system 744 generates a user-perceptible indication of at least one of a position and an orientation of the tracking sensor responsive to the sensor signal.

As used herein, the singular forms "a," "an", and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases and/or drawing labels such as "X-Y", "between X and Y" and "between about X and Y" can be interpreted to include X and Y.

As used herein, phrases and/or drawing labels such as "between about X and Y" can mean "between about X and about Y."

As used herein, phrases and/or drawing labels such as "from about X to Y" can mean "from about X to about Y."

It will be understood that when an element is referred to as being "on," "attached" to, "connected" to, "coupled" with, "contacting", "adjacent", etc., another element, it can be directly on, attached to, connected to, coupled with, contacting, or adjacent the other element or intervening elements may also be present. In contrast, when an element is referred to as being, for example, "directly on," "directly attached" to, "directly connected" to, "directly coupled" with, "directly contacting", or "directly adjacent" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper", "proximal", "distal", and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A guidewire, comprising:
    an elongate tube body defining a tube lumen and having longitudinally spaced proximal and distal body ends, the tube body including a first longitudinal biasing portion, including at least one first-direction circumferential helical cut therealong, and a second longitudinal biasing portion, including at least one second-direction circumferential helical cut therealong, the first direction being radially opposite the first direction;
    a core wire, at least partially located inside the tube lumen and having longitudinally spaced proximal and distal core wire ends; and
    a tracking sensor located at least partially within the tube lumen.

2. The guidewire of claim 1, wherein the tracking sensor is an electromagnetic coil sensor.

3. The guidewire of claim 1, wherein the tracking sensor is mounted to a predetermined mounting area of the core wire.

4. The guidewire of claim 1, wherein the tracking sensor is configured to provide a sensor signal, representative of the position and orientation of the tracking sensor and guidewire in three-dimensional space.

5. The guidewire of claim 4, wherein the sensor signal is provided to a navigation system configured to generate one or more output visualizations in a user-perceptible format.

6. The guidewire of claim 3, wherein the predetermined mounting area is a flatted plateau portion of the core wire.

7. The guidewire of claim 1, wherein an at least one signal wire includes a distal signal wire portion in electrical communication with the tracking sensor and a proximal signal wire portion located adjacent the proximal core wire end, the proximal signal wire portion having a U-shaped connection portion which has portions simultaneously laterally inside and outside the tube lumen, a terminating end of the proximal signal wire portion being attached to an outer surface of the tube body.

8. The guidewire of claim 7, wherein the terminating end of the proximal signal wire portion is compressed against the outer surface of the tube body by a conductive collar, the conductive collar being configured to selectively convey electrical signals between the proximal signal wire portion and an external guidewire control system.

9. The guidewire of claim 1, wherein the first and second longitudinal biasing portions are longitudinally spaced.

10. The guidewire of claim 9, including a transitional longitudinal portion longitudinally interposed between adjacent ones of the first and second longitudinal biasing portions, the transitional longitudinal portion including no helical cuts therein.

11. The guidewire of claim 1, including an outer coil surrounding the tube body adjacent the distal body end.

12. A surgical navigation system, comprising:
a guidewire including
an elongate tube body defining a tube lumen and having longitudinally spaced proximal and distal body ends, the tube body including a first longitudinal biasing portion, including at least one first-direction circumferential helical cut therealong, and a second longitudinal biasing portion, including at least one second-direction circumferential helical cut therealong, the first direction being radially opposite the first direction,
a core wire, at least partially located inside the tube lumen and having longitudinally spaced proximal and distal core wire ends, and
a tracking sensor located at least partially within the tube lumen and configured to provide a sensor signal; and
a communication device electrically coupled to the tracking sensor to receive the sensor signal;
wherein the surgical navigation system is configured to generate one or more output visualizations in a user-perceptible format.

13. The surgical navigation system of claim 12, wherein the communication device includes circuitry configured to amplify and/or digitize the sensor signal.

14. The surgical navigation system of claim 13, wherein the amplified and/or digitized signal is communicated from the communication device to the control unit, the control unit being configured to process the amplified and/or digitized signal according to application requirements.

15. The surgical navigation system of claim 12, wherein the communication device is configured to compute data indicating the position and orientation of the tracking sensor responsive to a sensor signal induced in the tracking sensor from an electromagnetic field generator and provide the computed data to a computer for additional processing.

16. The surgical navigation system of claim 12, wherein the outside communication device is configured to generate at least one three-dimensional user-perceptible virtual displays of patient anatomical geometry and the guidewire in real-time, responsive to the sensor signal, to facilitate intraoperative positioning of the guidewire relative to patient anatomy.

17. The surgical navigation system of claim 12, wherein the outside communication device is in wireless contact with the tracking sensor.

18. The surgical navigation system of claim 12, wherein an at least one signal wire includes a distal signal wire portion in electrical communication with the tracking sensor and a proximal signal wire portion located adjacent the proximal core wire end, the proximal signal wire portion having a U-shaped connection portion which has portions simultaneously laterally inside and outside the tube lumen, a terminating end of the proximal signal wire portion being attached to an outer surface of the tube body.

19. The surgical navigation system of claim 12, wherein the first and second longitudinal biasing portions are longitudinally spaced.

20. The surgical navigation system of claim 19, including a transitional longitudinal portion longitudinally interposed between adjacent ones of the first and second longitudinal biasing portions, the transitional longitudinal portion including no helical cuts therein.

21. The surgical navigation system of claim 12, wherein an at least one signal wire includes a distal signal wire portion in electrical communication with the tracking sensor and a proximal signal wire portion located adjacent the proximal core wire end, the proximal signal wire portion having a U-shaped connection portion which has portions simultaneously laterally inside and outside the tube lumen, a terminating end of the proximal signal wire portion being attached to an outer surface of the tube body.

22. The surgical navigation system of claim 21, wherein the terminating end of the proximal signal wire portion is compressed against the outer surface of the tube body by a conductive collar, the conductive collar being configured to selectively convey electrical signals between the proximal signal wire portion and an external guidewire control system.

* * * * *